US00PP25912P3

(12) United States Plant Patent
Stoppel

(10) Patent No.: US PP25,912 P3
(45) Date of Patent: Sep. 22, 2015

(54) CHERRY ROOTSTOCK PLANT NAMED 'STO3'

(50) Latin Name: ***Prunus cerasus* L.×*P.*×*schmittii* Rehder**
Varietal Denomination: STO3

(71) Applicant: Peter Stoppel Obstbau, Kressbronn (DE)

(72) Inventor: Peter Stoppel, Kressbronn (DE)

( * ) Notice: Subject to any disclaimer, the term of this patent is extended or adjusted under 35 U.S.C. 154(b) by 100 days.

(21) Appl. No.: 13/987,743

(22) Filed: Aug. 27, 2013

(65) Prior Publication Data

US 2014/0090120 P1 Mar. 27, 2014

(30) Foreign Application Priority Data

Sep. 24, 2012 (QZ) ..... PBR 2012/2007

(51) Int. Cl.
*A01H 5/06* (2006.01)
*A01H 5/08* (2006.01)

(52) U.S. Cl.
USPC ..... Plt./183
CPC ..... *A01H 5/085* (2013.01)

(58) Field of Classification Search
USPC ..... Plt./183
See application file for complete search history.

*Primary Examiner* — Anne Grunberg
(74) *Attorney, Agent, or Firm* — Myers Bigel Sibley & Sajovec, PA

(57) ABSTRACT

A new and distinct cultivar of *Prunus* plant named 'STO3,' characterized by its upright plant habit and typical hybrid growth; good adaptation to hot and dry conditions; and as a rootstock, slow vegetative growth imparts uniformity, higher yield and better fertility to the grafted variety as compared to a standard rootstock such as Gisela 5, F12/1 and Mazzard.

3 Drawing Sheets

Latin name of the genus and species: The Latin name of the genus and species of the plant variety disclosed herein is *Prunus cerasus* L.×*P.*×*schmittii* Rehder.

Variety denomination: The inventive cultivar of *Prunus cerasus* L.×*P.*×*schmittii* Rehder disclosed herein has been given the varietal denomination 'STO3.'

RELATED APPLICATION INFORMATION

This application claims priority to European Community Plant Variety Application No. 2012/2007, filed Sep. 24, 2012; the disclosure of which is incorporated herein by reference in its entirety.

BACKGROUND OF THE INVENTION

The present invention relates to a new and distinct cultivar of *Prunus* plant, typically used as a cherry tree rootstock, botanically known as *P Prunus cerasus* L.×*P.*×*schmittii* Rehder, and hereinafter referred to by the name 'STO3.'

The new and distinct variety of cherry hybrid tree of the present invention was bred as a cross of *Prunus cerasus* with a *Prunus canescens* hybrid in Germany in 1989. It has been successfully asexually propagated by tissue culture. The purpose of breeding program was to find a better adapted cherry rootstock. The new *Prunus* plant is better adapted to heat and aridity than other rootstocks with a slow vegetative growth. The breeder has succeeded in creating a new cherry rootstock, which has a higher yield and influences the grafted variety positively in fertility.

SUMMARY OF THE INVENTION

Plants of the new *Prunus* have not been observed under all possible environmental conditions. The phenotype may vary slightly with variations in environment such as temperature and light intensity without any variance in genotype.

The following traits have been repeatedly observed and are determined to be the unique characteristics of 'STO3.' These characteristics in combination distinguish 'STO3,' as a new and distinct cultivar of *Prunus:*

1. Upright plant habit;
2. Typical hybrid growth;
3. Good adaptation to hot and dry clime conditions;
4. As a rootstock, with moderate vegetative growth, it produces a dwarf tree;
5. As a rootstock, imparts uniformity and higher yield to the grafted variety;
6. 40% less vigour compared to *Prunus avium* seedlings; and
7. Absence of suckers.

As used herein, "higher yield" refers to the impact of the rootstock of the tree on both vegetative as well as generative growth. Thus, the rootstock can affect the generative growth and assist the grafted species to achieve greater yield. Therefore, with regard to 'STO3,' the yield per tree and crown volume is higher than that of a standard rootstock such as Gisela 5, F12/1 and Mazzard.

Further with 'STO3' as the rootstock, the grafted variety can achieve better fertility (i.e., greater generative growth). That is, use of 'STO3' as a rootstock results in greater generative growth than in the case of standard rootstock (Gisela 5, F12/1, Mazzard); the tree produces more flowers, more fruit, with a greater yield of the same or larger fruit size. In the end greater output is achieved.

The parents of 'STO3' are partly a hybrid between *Prunus avium* and *Prunus canescens* and partly a *Prunus cerasus*—wild species (all of which are unnamed and not patented). The parent (*Prunus avium*×*Prunus canescens*) and the parent

*Prunus cerasus* each have a brownish wood, while the new hybrid ('STO3') has a greyish wood with a distinctive lenticel grain. Further, the parent *Prunus cerasus* has a clearly oval leaf (broadest in the middle), while the lower third of the 'STO3' leaf bulges and ends in a very sharp tip.

Plants of the new *Prunus* also can be compared to plants of *Prunus* 'Weiroot 720' (U.S. Plant Pat. No. 22,867, issued Jul. 24, 2012). In side-by-side comparisons conducted in Kressbronn, Germany, plants of the new *Prunus* differed primarily from plants of 'Weiroot 720' in the following characteristics:

1. As a rootstock, plants of the new *Prunus* have about double the growth in comparison to plants with 'Weiroot 720' rootstocks;
2. Plants of the new *Prunus* have hairy one-year-old shoots, whereas 'Weiroot 720' has a hairless one-year-old shoot;
3. Plants of the new *Prunus* have hairs on the lower surface from the leaves, whereas 'Weiroot 720' does not have any hairs on the lower surface from the leaves; and
4. Due to its typical hybrid growth, plants of the new *Prunus* impart higher yield to the scion plant than plants of 'Weiroot 720.'

'STO3' was first asexually propagated in autumn 2001 in Freising, Germany, using tissue culture. Asexual reproduction of *Prunus* rootstock plant 'STO3' by tissue culture since autumn 2001 has shown that the unique features of this new variety are stable and the plant reproduces true to type in succeeding generations of asexual reproduction.

BRIEF DESCRIPTION OF THE DRAWINGS

The accompanying photographs illustrate the overall appearance of the new *Prunus* plant. These photographs show the colors as true as it is reasonably possible to obtain in colored reproductions of this type. Colors in the photographs may differ slightly from the color values cited in the detailed botanical description which accurately describe the colors of the new *Prunus* plant.

DETAILED BOTANICAL DESCRIPTION

Figure 1:
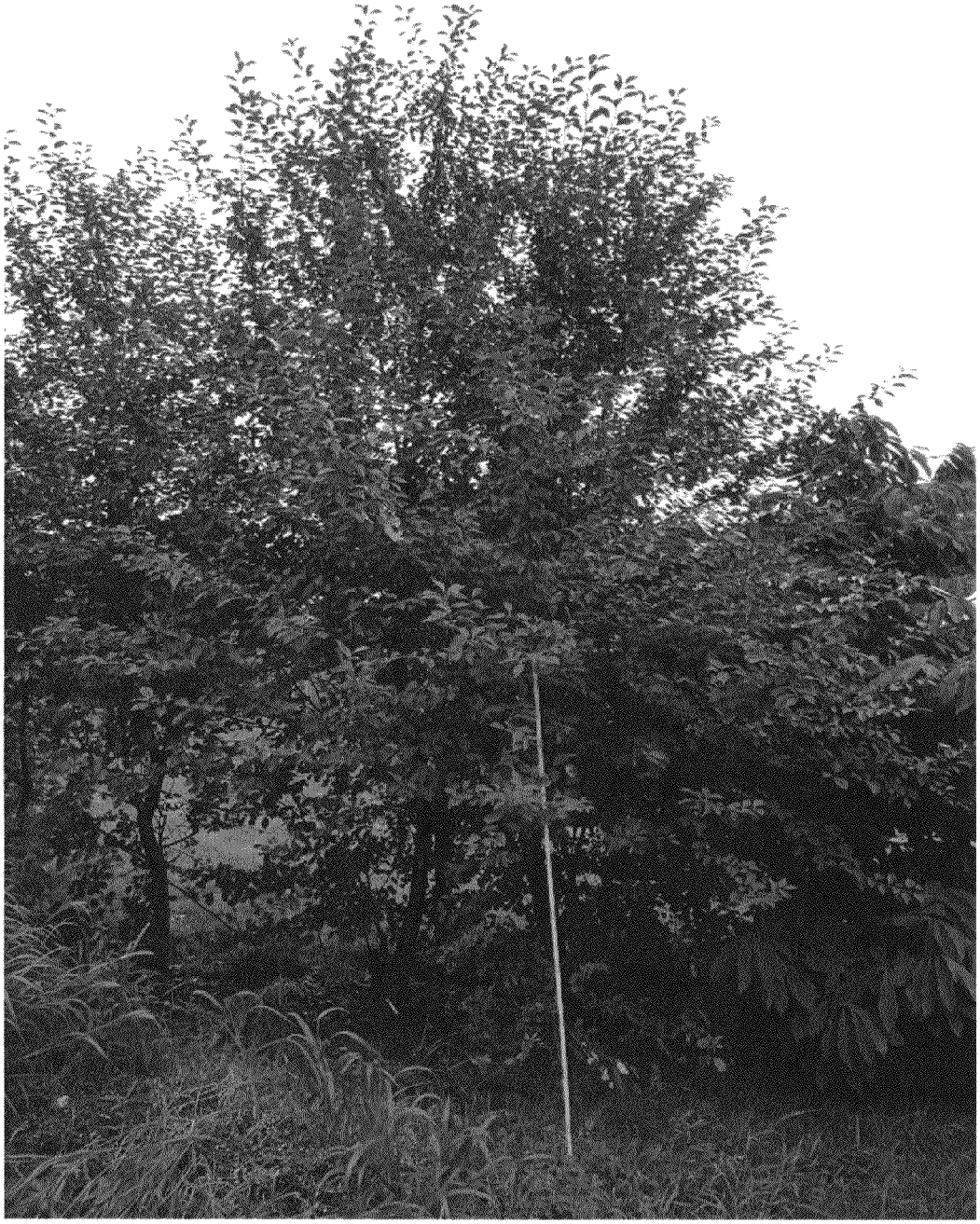
FIG. 1 provides a side perspective view of a typical tree of 'STO3' grown in an outdoor orchard.
Figure 2:
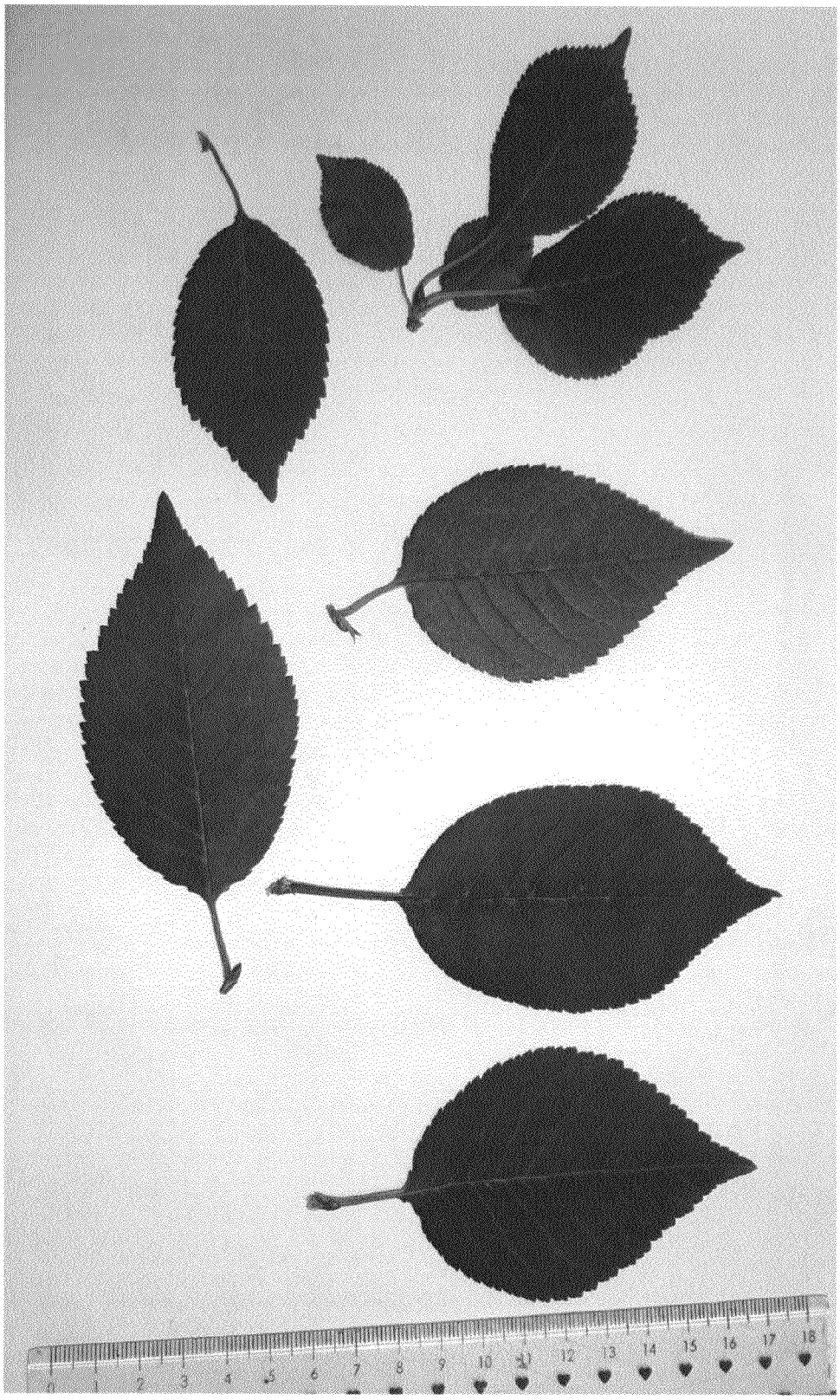
FIG. 2 provides a close-up view of leaves of 'STO3'.
Figure 3:
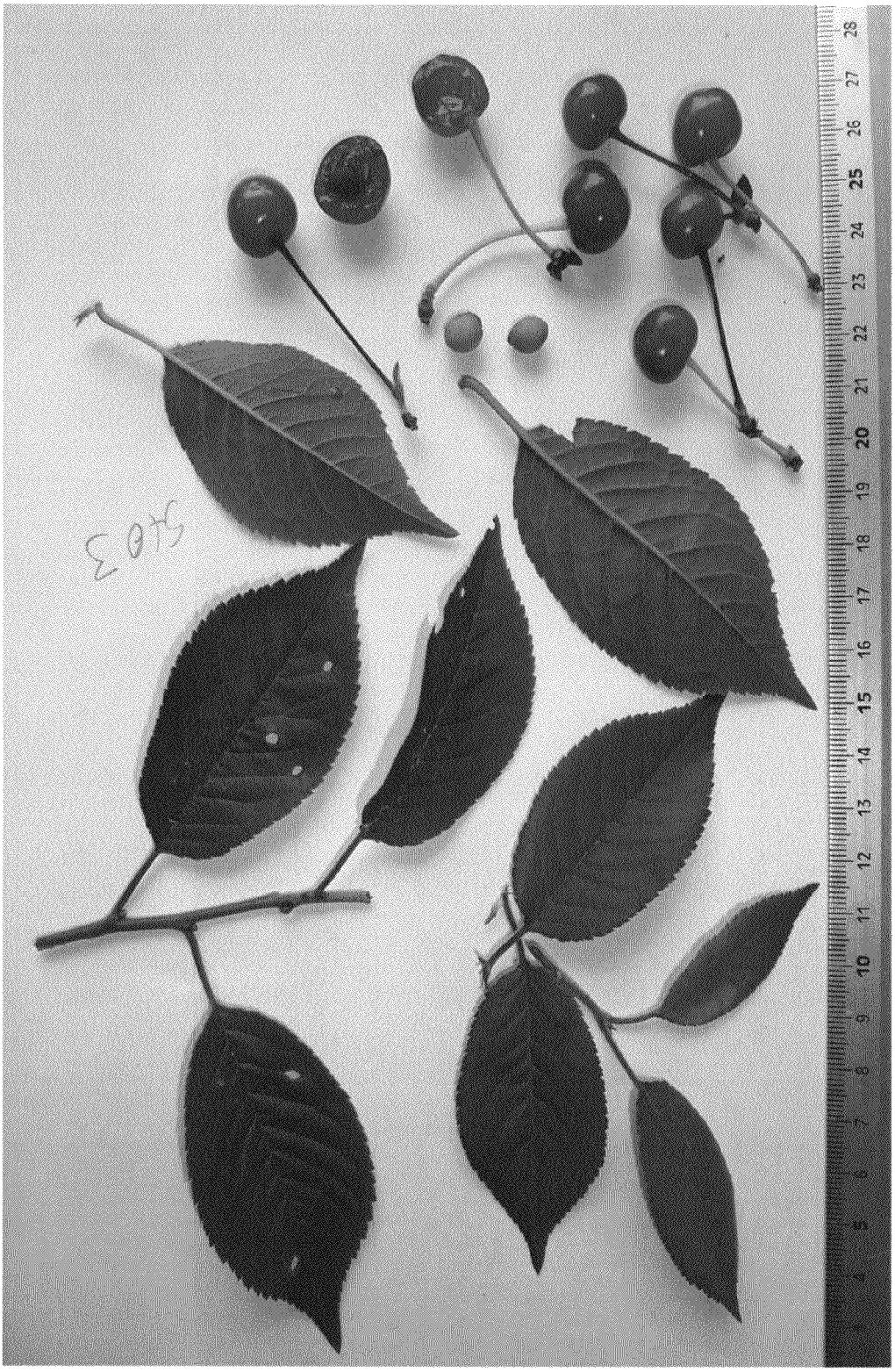
FIG. 3 provides a close-up view of fruits, branches and leaves of 'STO3.'

The aforementioned photographs, following observations and measurements describe plants grown during the summer in Kessbronn, Germany in an outdoor orchard and under conditions and practices generally used in commercial cherry production. Plants were 11 years old when the photographs and descriptions were taken. Measurements and numerical values represent averages for typical plants and plant parts. The actual measurements of any individual plant or plant parts, or any group of plants or plant parts, of the new *Prunus* plant may vary from the stated average. In the following description, color references are made to The Royal Horticultural Society (R.H.S.) Colour Chart, except where general terms of ordinary dictionary significance are used.

'STO3' is generally erect and medium strong in growth. The hybrid growth is typical for the new *Prunus* plant. After eleven growing seasons in Kressbronn, Germany, a height of about 5.6 meters, a width of about 3.5 meters and a trunk diameter of about 13 cm were observed for 'STO3.' The growth reduction induced by 'STO3' allows a highly intensive cherry production with dwarf trees.

Botanical classification: *Prunus cerasus* L.×*P.*×*schmittii* Rehder 'STO3.'

Parentage: Breeding between *Prunus cerasus* and a *Prunus canescens* hybrid.

Propagation:

*Type*.—By asexual reproduction.

*Method*.—By tissue culture since the autumn of 2001 in a controlled environment. The process is similar to the propagation of other cherry rootstock.

Plant description:

*Plant and growth habit*.—Used a rootstock; upright plant habit; plants are typically grown as a single stem; moderate vigor.

*Stem description*.—Strength: Strong. Texture: Rough. Color: Grey brownish RHS 199B.

*Leaf description, fully developed leaves*.—Arrangement: Alternate; simple. Length: About 5.8 cm to about 7.2 cm. Width: About 3.5 cm to about 4 cm. Shape: Elliptic to ovate, moderately elongated. Apex: Acute. Tip: Acuminate. Base: Obtuse. Margin: Biserrate. Texture, upper surface: Glabrous. Texture, lower surface: Coarse, pubescent. Color: Fully developed leaves, upper surface: Close to RHS 136A; venation, close to RHS 146C. Fully developed leaves, lower surface: Close to RHS 137C; venation, close to RHS 152D.

*Petiole description*.—Length: About 1 cm to about 1.6 cm. Diameter: About 0.16 cm. Color, upper surfaces and lower surfaces: Close to RHS163A.

*Presence of stipules*.—Present. Frequency: Not at every bud.

*Stipule description*.—Length: About 0.6 cm to about 1 cm. Width: About 0.3 cm. Shape: Triangular, very elongated. Margin: Erose.

Flower description:

*Flower type/habit*.—3 to 6 flowers single flowers arranged on compound panicles. Flowers occur in general on one year old branches.

*Fragrance*.—Weak, pleasant.

*Natural flowering season*.—In April in south Germany, three days before 'Weiroot 720' (U.S. Plant Pat. No. 22,867).

*Lastingness of entire bloom period*.—About 15 days.

*Lastingness of an individual bloom*.—About 8 days.

*Inflorescence height*.—About 4 cm to about 4.6 cm.

*Inflorescence diameter*.—About 5 cm to about 9 cm.

*Flower diameter*.—About 2.4 cm to about 3.1 cm.

*Flower depth*.—About 1.2 cm to about 1.5 cm.

*Bud length*.—6-10 mm.

*Bud width* (*bud diameter*).—3-5 mm.

*Bud shape*.—Cylindrical, tapering (obtusely pointed) at the protruding end.

*Bud colour*.—Brown to reddish brown -RHS- 1683A.

*Petals*.—Arrangement: Five petals in a single whorl. Length: About 1.2 cm to about 1 cm. Width: About 1 cm to about 1.2 cm. Arrangement: Slightly overlapping. Shape: Oblong, slightly elongated. Apex: Rounded, slightly elongated. Base: Truncate. Margin: Entire. Texture, upper and lower surfaces: Smooth, glabrous. Color: When fully opened, upper surface: Close to RHS 155B. When opening and fully opened, lower surface: Close to RHS 155B.

*Sepals*.—Arrangement: Five sepals in a single whorl. Length: About 0.4 cm. Width: About 0.3 cm. Shape: Triangular, moderately elongated. Apex: Pointed.

Base: Truncate. Margin: Entire. Texture, upper and lower surfaces: Smooth, glabrous. Color, upper surfaces: Close to RHS 142B. Color, lower surfaces: Close to RHS 145B.

*Pedicels*.—Length: About 2.3 cm to about 2.6 cm. Diameter: About 0.1 cm. Angle: About intermediate to semi-prostrate from the inflorescence stalk. Texture: Smooth, glabrous. Color: Close to RHS 142A.

*Peduncle*.—Length: About 0.1 cm. Diameter: About 0.2 cm. Surface: Smooth. Color: Close to RHS 149A.

*Reproductive organs*.—Stamens: Quantity per flower: Numerous. Filament length: About 5 mm to 12 mm. Filament color: Close to RHS 155B. Anther length: About 0.3 mm to about 1 mm. Anther color: Close to RHS 6A. Pollen color: Close to RHS 6D. Pistils: Quantity per flower: One. Pistil length: About 10 mm to about 13 mm. Style length: About 8 mm to about 11 mm. Style color: Close to RHS 150C. Stigma shape: Round. Stigma color: Close to RHS 149A.

*Fruit description*.—Maturity when described. Date picking: July in south Germany, varies with climatic conditions: About the same time as 'Weiroot 720' or about three days later. Size: Small, about 1.3 cm to about 1.6 cm diameter. Average weight: about 1.5 g, varies slightly with fertility of the soil, amount of thinning and climatic conditions. Form: Globose, Slightly flat at the apex. Stem cavity: Slightly obcordate to flat. Color: RHS 40A.

*Peduncle description*.—Size: Average length about 3.6 cm. Average diameter about 0.1 cm. Color: RHS 149A.

*Stone description*.—Average length: about 0.8 cm. Average width: about 0.75 cm. Average thickness: about 0.66 cm. Form: Nearly globose. Base: Flat. Apex: Rounded. Color: RHS 164C when dry.

*Fruit use*.—Not be used as a dessert fruit.

Pollination requirements: 'STO3' is not self-fertile and requires a pollinator.

Temperature tolerance: Plants of the new *Prunus* have been observed to tolerate temperatures from about −20° C. to about 40° C. Notably, under hot and dry climate climatic conditions, 'STO3' trees do not exhibit chlorosis. These trees are very robust in the presence of substantial variations in temperature (very low temperatures in winter (−20° C.) and very hot temperatures in summer (+40° C.)) and such temperature fluctuations have no negative effect on the trees.

Drought tolerance: Due to a deep root system, the new variety, 'STO3,' is tolerant to drought conditions.

What is claimed is:

1. A new and distinct cultivar of *Prunus cerasus* L.×*P.*× *schmittii* Rehder plant named 'STO3,' substantially as illustrated and described herein.

* * * * *

UNITED STATES PATENT AND TRADEMARK OFFICE

CERTIFICATE OF CORRECTION

PATENT NO. : PP25,912 P3
APPLICATION NO. : 13/987743
DATED : September 22, 2015
INVENTOR(S) : Peter Stoppel It is certified that error appears in the above-identified patent and that said Letters Patent is hereby corrected as shown below:

On Title Page:
Item (30), Foreign Application Priority Data:
Please correct "(QZ).....PBR 2012/2007"
to read -- (EP).....PBR 2012/2007 --

Signed and Sealed this
Seventeenth Day of May, 2016

Michelle K. Lee

Michelle K. Lee
*Director of the United States Patent and Trademark Office*